United States Patent [19]

Bakshi et al.

[11] 4,259,246

[45] Mar. 31, 1981

[54] MALEIC ANHYDRIDE PRODUCTION WITH RECYCLE TREATMENT

[75] Inventors: Kiran R. Bakshi, El Cerrito; David M. Marquis, Lafayette; Stephen G. Paradis, Fairfax, all of Calif.

[73] Assignee: Chevron Research Company, San Francisco, Calif.

[21] Appl. No.: 84,978

[22] Filed: Oct. 15, 1979

Related U.S. Application Data

[63] Continuation of Ser. No. 645,584, Dec. 31, 1975, abandoned.

[51] Int. Cl.$^3$ .............................................. C07D 307/60
[52] U.S. Cl. .................................. 260/346.75; 562/549
[58] Field of Search ..................................... 260/346.75

[56] References Cited

U.S. PATENT DOCUMENTS

| | | | |
|---|---|---|---|
| 3,891,680 | 6/1975 | Katsumoto et al. | 260/346.75 |
| 3,904,652 | 9/1975 | Frank | 260/346.75 |
| 3,907,833 | 9/1975 | Slinkard et al. | 260/346.75 |

*Primary Examiner*—Henry R. Jiles
*Assistant Examiner*—Bernard Dentz
*Attorney, Agent, or Firm*—D. A. Newell; T. G. DeJonghe; C. J. Caroli

[57] ABSTRACT

A process for producing maleic anhydride from a $C_4$ hydrocarbon selected from n-butane and n-butene feed which comprises: (a) feeding the $C_4$ hydrocarbon and air to a reactor; (b) contacting the $C_4$ hydrocarbon and air in the reactor with a catalyst comprising vanadium and phosphorus oxides at reaction conditions including a temperature between 550° and 1000° F. so as to obtain a reactor effluent containing maleic anhydride, unreacted butane, nitrogen, oxygen, and acrylic, acetic or maleic acid or mixtures of the foregoing acids; (c) removing maleic anhydride from the reactor effluent to obtain maleic anhydride-lean effluent; (d) removing said acids from at least a portion of the maleic anhydride-lean effluent to obtain a purified recycle stream containing less than 100 ppm of the acids; and (e) recycling the purified stream to the reactor. Preferably the acids are removed in step (d) by water and/or caustic scrubbing the maleic anhydride-lean effluent.

4 Claims, 1 Drawing Figure

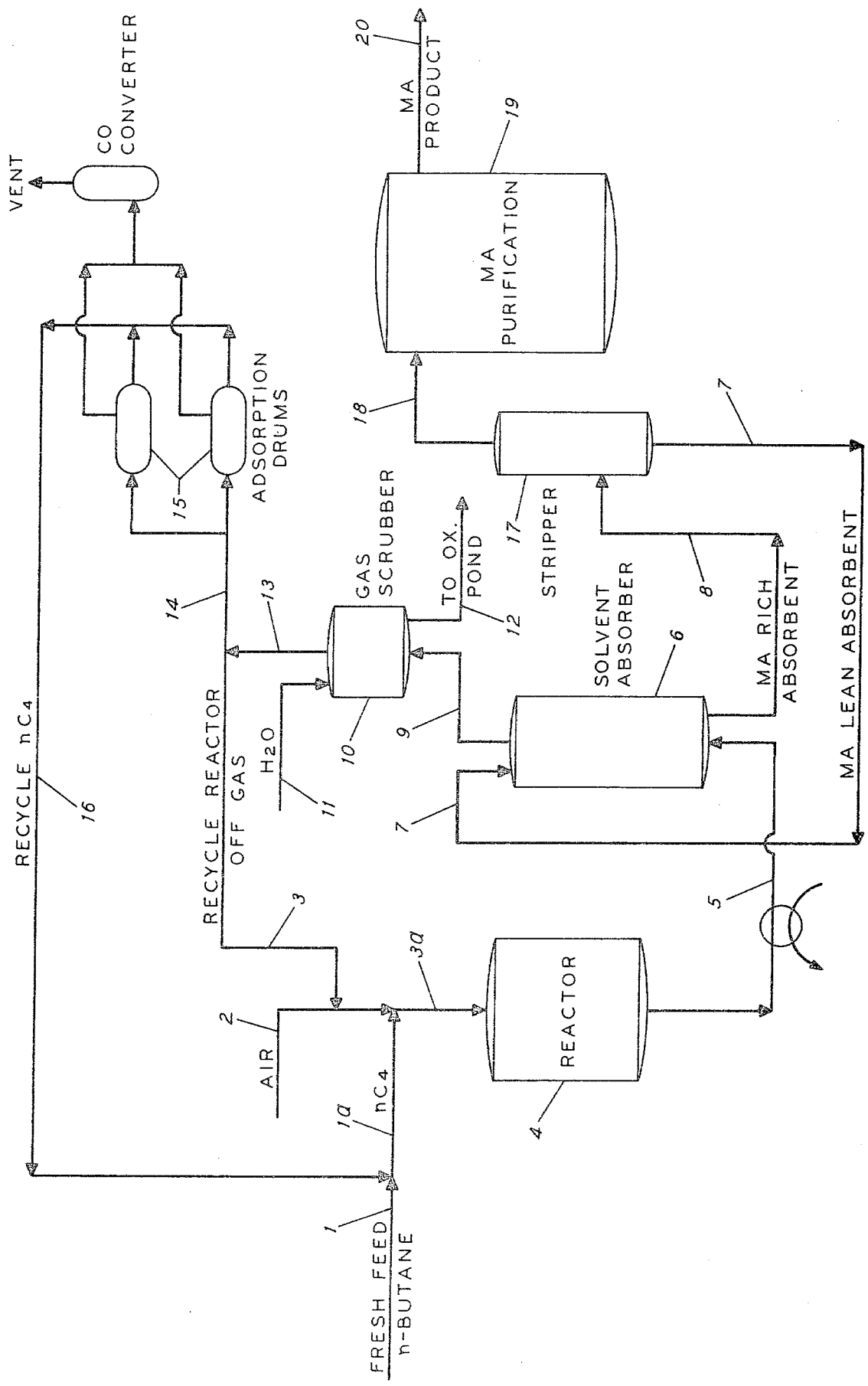

MALEIC ANHYDRIDE PRODUCTION WITH RECYCLE TREATMENT

This is a continuation of application Ser. No. 645,584, filed Dec. 31, 1975, and now abandoned.

RELATED APPLICATION

This application is related to our commonly assigned and concurrently filed application Ser. No. 645,585, entitled "Maleic Anhydride Production", which application is incorporated herein by reference.

BACKGROUND OF THE INVENTION

The present invention relates to the oxidation of a butane feed to maleic anhydride.

Oxidation of hydrocarbons to maleic anhydride is well known. Feeds which have been disclosed include benzene, butene, and n-butene. A series of patents to Kerr, including U.S. Pat. Nos. 3,156,705, 3,156,706, 3,156,707, 3,238,254, 3,255,211, 3,255,212, 3,255,213, 3,288,721, 3,351,565 and 3,385,796, discloses vanadium-phosphorus oxide catalysts for oxidation of butene to maleic anhydride.

Friedrichsen et al U.S. Pat. No. 3,478,063 discloses oxidation of olefinically unsaturated hydrocarbons with a catalyst containing vanadium and phosphorus oxides and wherein the amount of phosphorus oxide is at least equal to twice that of the vanadium oxide and wherein the catalyst contains at least one other oxide of chromium, iron, cobalt or nickel, and the catalyst is preferably on a carrier. The patent discloses at Col. 4 that the catalyst may have a surface area from 1 to 100 $m^2/g$.

Bergman U.S. Pat. No. 3,293,268 discloses a vanadium-phosphorus oxide catalyst for oxidation of butane to maleic anhydride. Surface area is not disclosed for the catalyst in the Bergman reference. Also, as in the Friedrichsen et al reference, the Bergman catalyst is prepared by an aqueous solution method.

Schneider U.S. Pat. No. 3,864,280 discloses a vanadium-phosphorus mixed oxide catalyst having an intrinsic surface area of 7 to 50 $m^2/g$. The Schneider catalyst can be prepared using an organic medium as opposed to an aqueous medium.

The use of recycle of unreacted constituents to a reactor is, of course, well known and frequently is employed in various processes.

Bissot et al, in "Oxidation of Butane to Maleic Anhydride", IEC Vol. 2, No. 1, March 1963, pp. 57–60, disclose that, in a process for conversion of butane to maleic anhydride unreacted butane may be recycled to the reactor. However, Bissot et al prefer to use sequential reaction, with maleic anhydride separation between the reactors, and with unreacted butane from the first reactor being fed to the second reactor, etc.

U.S. Pat. No. 3,904,652 discloses the oxidation of n-butane to maleic anhydride using enriched oxygen and with a recycle stream of reactor effluent which lowers the oxygen concentration in the total feed to the reactor. It is known that explosive mixtures of butane and oxygen exist and that some oxygen concentrations can cause an oxygen-butane-nitrogen mixture to go into the explosive range; see, for example, Bureau of Mines Bulletin 503 (1952), FIG. 35, page 62, and Bureau of Mines Bulletin 627 (1965), FIG. 21, page 23. In U.S. Pat. No. 3,904,652, the reactor feed mixture is kept below explosive (flammable) limits by the addition of an inert gas, e.g., nitrogen, to the enriched oxygen fresh feed.

Butane conversion levels in U.S. Pat. No. 3,904,652 are 30 to 70% per pass. The unconverted butane passes out of the oxidizer reactor as part of the reactor effluent. The effluent is processed to remove maleic anhydride. The maleic anhydride is removed from the effluent in part by cooling to condense out liquid maleic anhydride. Completion of maleic anhydride removal from the effluent is carried out by scrubbing the vapor/gaseous material left from the condensation step. The scrubbing is done by contacting the effluent with a recirculated aqueous maleic acid solution to which is added an undisclosed amount of fresh water. The maleic anhydride-free gaseous effluent is then divided into two parts, a recycle stream which is recycled back to the reactor, and a purge stream which is removed from the system.

SUMMARY OF THE INVENTION

According to the present invention, a process is provided for producing maleic anhydride from a $C_4$ hydrocarbon selected from n-butane and n-butene fuel which comprises: (a) feeding the $C_4$ hydrocarbon and air to a reactor; (b) contacting the $C!4$ hydrocarbon and air in the reactor with a catalyst comprising vanadium and phosphorus oxides at reaction conditions including a temperature between 550° and 1000° F. so as to obtain a reactor effluent containing maleic anhydride, unreacted butane, nitrogen, oxygen, and acrylic, acetic, or maleic acid or mixtures of the foregoing acids; (c) removing maleic anhydride from the reactor effluent to obtain maleic anhydride-lean effluent; (d) removing said acids from at least a portion of the maleic anhydride-beam effluent to obtain a purified recycle stream containing less than 100 ppm of the acids; and (e) recycling the purified stream to the reactor.

Among other factors, the present invention is based on our finding that surprisingly improved n-butane feed conversion and also selectivity of the conversion to maleic anhydride are achieved in a recycle operation if acids are removed from the recycle down to a low level below at least 100 ppm. We have found, for instance, that when a stream is taken directly from the effluent of the oxidation reactor and is recycled back to the reactor (or to a similar reactor), the conversion and selectivity are deleteriously affected. One might have assumed that since the effluent, of course, comes from the oxidation reactor itself, simply putting a portion of this effluent back to the reactor would not have any substantial and prompt effect, but we have found to the contrary.

Preferably the acids are removed in step (d) of the above process by water or aqueous caustic solution scrubbing the maleic anhydride-lean effluent. The water scrubbing can be carried out, for instance, using an absorption column wherein the maleic anhydride-lean effluent is contacted countercurrently with water to thereby absorb and remove acids from the maleic anhydride-lean effluent prior to recycling the maleic anhydride-lean effluent to the reactor. The water, and/or aqueous basic solution such as sodium or potassium hydroxide, carbonate, or bicarbonate must be used in an amount and purity (or base concentration) sufficient to remove the acids in sufficient amount so that the maleic anhydride-lean effluent which is recycled to the reactor contains no more than 100 ppm of the acids. Preferably the scrubbed effluent is treated with sufficient water or other means for removing light acids so that the acid content is reduced to less than 10 ppm, and still more preferably less than 7 ppm. The use of a water scrubbing system which already contains substantial amounts of acids, such as in the case of a recirculated maleic acid aqueous solution, is thus not desirable as such a solution is ineffective or of substantially reduced effectiveness to remove light acids down to a very low level in the resultant scrubbed maleic anhydride-lean effluent.

In addition to the removal of acids from the reactor recycle stream, usually and preferably other partially oxidized by-products, such as formaldehyde, are removed so that the recycle stream contains no more than 100, preferably no more than 10, and still more preferably no more than 7, ppm partially oxidized by-products such as the light acids and formaldehyde.

Unless otherwise indicated, the parts per million acids or other partially oxidized by-products in the purified effluent are by weight. The terminology "partially oxidized" is used in contrast to carbon oxides which result from completely oxidizing the $C_4$ hydrocarbon feed.

In the process of the present invention, rather than the use of a condensation-aqueous maleic anhydride recovery system, it is preferred to recover the maleic anhydride from the reactor effluent to obtain in maleic anhydride-lean effluent solely by countercurrently contacting the reactor effluent with an organic absorbent. The maleic anhydride is then recovered from the organic absorbent by conventional absorbent stripping methods. Suitable organic absorbents include benzophenones such as the polymethylbenzophenones, e.g., di-, tri- and tetramethylbenzophenone, as disclosed in commonly assigned application Ser. No. 550,070 entitled "Anhydride Separation Process" and now abandoned.

Preferred operating conditions for the oxidation reactor are as follows:

|  | Preferred | More Preferred | Most Preferred |
| --- | --- | --- | --- |
| Temperature, °F. | 650–950 | 700–850 | 700–800 |
| Pressure, psig | 10–1000 | 20–50 | 25–40 |
| Space rate, VHSV[1] | 1000–10,000 | 2000–5000 | 3500–4500 |
| Feed n-butane content, Combined fresh + recycle feed. vol. % | 1–5 | 1.5–4 | 2–3.5 |
| % effluent recycled directly (remainder of effluent n-butane recycled after separation from other effluent gases) | 20–95 | 65–90 | 80 |

[1]Total volume of gas at 70° F. and 1 atm. per hour per cubic foot of catalyst volume.

Preferred catalysts for use in the present invention are high-activity, high-surface-area vanadium-phosphorus oxide catalysts, preferably having an intrinsic surface area between about 7 and 50 $m^2/g$.

Particularly preferred catalysts for use in the process of the present invention are those disclosed in Schneider U.S. Pat. No. 3,864,280, specifically crystalline phosphorus-vanadium mixed oxide catalysts containing pentavalent phosphorus, vanadium and oxygen, said vanadium having an average valence in the range from about +3.9 to +4.6, said oxide having a phosphorus-to-vanadium atomic ratio in the range from about 0.9–1.8 to 1, and an intrinsic surface area in the range from about 7 to 50 $m^2/g$.

As defined in U.S. Pat. No. 3,864,280, the term "intrinsic surface area" is used herein to mean the surface area of the mixed vanadium-phosphorus oxide material itself, i.e., per se, in the absence of a support or carrier.

The catalysts of U.S. Pat. No. 3,864,280 are particularly suited for use in the process of the present invention, and the disclosure of U.S. Pat. No. 3,864,280 is incorporated herein by reference.

Preferred operating conditions for removal of the acids from the maleic anhydride-lean reactor effluent by use of water scrubbing are as follows:

|  | Preferred | More Preferred |
| --- | --- | --- |
| Water feed rate to maleic anhydride-lean effluent feed rate, q/std. $ft^3$ | 1 to 100 | 1 to 25 |
| Countercurrent contacting stages, theoretical stages | 1 to 25 | 1 to 10 |
| Fresh water feed temperature, °F. | 50 to 120 | 50 to 80 |
| Operating pressure, psig | 0 to 1000 | 5 to 40 |

BRIEF DESCRIPTION OF THE DRAWING

The drawing is a schematic process flow diagram illustrating a preferred embodiment of the present invention.

FURTHER DESCRIPTION OF THE DRAWINGS AND EXAMPLES

Example 1

Feed butane in line 1a, made up from 97 lbs/hr of fresh-feed butane in line 1 and 36 lb/hr of recycled butane in line 16 is mixed with about 1426 lbs/hr of fresh make-up air introduced via line 2, and about 5995 lbs/hr of recycled off-gas, and the mixture is introduced into oxidizer reactor 4. The oxidizer reactor consists of conventional heat exchanger-type design with catalyst packed in tubes surrounded by a heat-transfer liquid (a "salt bath"). The reaction mixture is oxidized in the presence of a catalyst effective for accelerating the reaction of n-butane with air to form maleic anhydride. Preferred catalysts comprise mixed oxides of vanadium and phosphorus, especially those described in the previously cited U.S. Pat. No. 3,864,280, and preferred reaction temperatures are in the range 700°–800° F.

Following oxidation, the gaseous effluent flows through line 5 into absorber 6. About 104 lbs/hr of maleic anhydride is absorbed in the organic solvent flowing into the absorber from line 7. The gaseous stream, 7450 lbs/hr, leaves the absorber through line 9 at a temperature of about 160° F. and is given a water wash in vessel 10. The solvent-maleic anhydride stream leaves the absorber through line 8 for maleic anhydride stripping and further purification of the crude product.

The remaining 7450 lbs/hr of the maleic anhydride-lean stream 9 is washed in countercurrent water scrubber 10 using fresh water to remove the unabsorbed acids. In a typical single-stage scrubber, about 21,900 lbs/hr of fresh water removes about 3–4 lbs/hr of light acids (acetic, acrylic, maleic and traces of butyric and the like) and unabsorbed maleic anhydride. The water requirements may be reduced by use of a multi-stage scrubber. The acid content of the 7331 lbs/hr stream 13 is below about 10 ppm, specifically about 6 ppm, in this mode of operation.

Washed off-gas leaving the water wash at a temperature of about 100° to 120° F. is split into streams 3 and 14. About 5995 lbs/hr of this washed off-gas is compressed and recycled back to the oxidizer through line 3 and the remaining 1336 lbs/hr of off-gas is passed through line 14 for butane recovery in adsorber 15.

Butane in line 14 is adsorbed in the adsorber by a cyclic operation using multiple beds filled with adsorbents such as activated carbon. The denuded off-gas, 1300 lbs/hr, mainly containing oxygen, nitrogen and oxides of carbon, is vented out and the butane adsorbed on the adsorbant is recovered by suitable desorption such as steaming at about 250° F. followed by condensation and phase separation. The recovered butane, 36 lbs/hr, is then recycled back through line 16 to the reactor.

To reduce the amount of aqueous scrubbing solution and/or to obtain more nearly complete removal of the acids from the recycle portion of the reactor effluent, a solution of sodium or potassium hydroxide, carbonate, or bicarbonate in water is advantageously used in place of simply water.

Example 2

The process was carried out as in Example 1, with single-stage scrubbing of the maleic anhydride-lean off gas to remove light acids from the recycle to the reactor.

The effects of acid contaminants in a reactor feed were tested in a separate test reactor (as we did not want to vary conditions in our main reactor) using the same type catalyst that was used in the main reactor. The reactant feed to this test reactor consisted of a slipstream from either stream No. 5 or 13 of FIG. 1. When the test reactor feed is obtained from stream 13, the test reactor was exposed to a washed off gas consisting of butane, oxygen, nitrogen and carbon oxides with only minute traces of light acids (about 6 ppm). The rate data obtained for the first run (see Run No. 1 in Table I below) was used for further comparison.

Subsequent test runs consisted of alternately switching the test reactor feed to slipstreams from streams 5 and 13 and evaluating the test reactor performance for each such run.

The performance of the test reactor under these conditions is shown in Table I. It is to be noted that the presence of acid contaminants in the feed immediately dropped the catalyst activity and selectivity for maleic anhydride production. See Run No. 2 in Table I. Also, this deleterious effect was found irreversible with removal of the feed contaminants in the subsequent test run. See Run No. 3 in Table I. The performance of the catalyst continues to degrade as it is further treated with an acid-contaminated stream. See Run No. 4, second exposure to stream No. 5.

A rather surprising finding of these experiments is that the presence of acid contaminants in the feed increases the light acid production rate in the subsequent test runs. In a recycle operation with less effective removal of acid contaminants from the recycled effluent stream, this deleterious effect assures a continued, accelerated degradation of the catalyst performance. Thus, it is especially advantageous to remove the light acids in accordance with the process of the present invention. Further experiments with a synthetic feed containing butane with either acetic or acrylic acid in the absence of maleic anhydride confirm the deleterious effect observed using stream 5.

TABLE I

Effect of Acid-Contaminants on Catalyst Performance In Test Reactor

| Feed Slip Stream | Relative Rates | | |
|---|---|---|---|
| | Butane Oxidation | MA Production | Light Acids Production |
| (1) Initial, portion of stream 13 used as test reactor feed (Reference run) | 100 | 100 | 100 |
| (2) After first exposure of test reactor catalyst to a portion of stream 5* | 65 | 65 | 128 |
| (3) Repeat feed of purified stream 13 to test reactor | 91 | 92 | 157 |
| (4) Second exposure to stream No. 5* | 61.4 | 59.7 | 171 |
| (5) Repeat feed of stream No. 13 to test reactor | 73.8 | 69.4 | 214 |

*Contaminants Contents:
MA 1.38% (wt)
Acetic Acid 660 ppm
Acrylic Acid 330 ppm

What is claimed is:

1. A process for producing maleic anhydride from a $C_4$ hydrocarbon selected from n-butane and n-butene feed which comprises:
   (a) feeding the $C_4$ hydrocarbon and air to a reactor;
   (b) contacting the $C_4$ hydrocarbon and air in the reactor with a catalyst comprising vanadium and phosphorus oxides, said vanadium having an average valence in the range from about +3.9 to 4.6, and said oxides having a phosphorus-to-vanadium atomic ratio in the range from about 0.9–1.8 to 1, at reaction conditions including a temperature between 550° and 1000° F. so as to obtain a reactor effluent containing maleic anhydride, unreacted $C_4$ hydrocarbon, nitrogen, oxygen, and acrylic, acetic or maleic acid or mixtures of the foregoing acids;
   (c) removing maleic anhydride from the reactor effluent to obtain maleic anhydride-lean effluent;
   (d) removing said acids from at least a portion of the maleic anhydride-lean effluent to obtain a purified recycle stream containing less than 100 ppm of the acids by scrubbing the maleic anhydride-lean effluent with water or an aqueous solution of base; and
   (e) recycling the purified stream to the reactor.

2. A process in accordance with claim 1 wherein the $C_4$ hydrocarbon feed is n-butane.

3. A process in accordance with claim 2 wherein the maleic anhydride is removed from the reactor effluent to obtain the maleic anhydride-lean effluent solely by countercurrent contacting of the reactor effluent with an organic absorbent to thereby absorb the maleic anhydride into the organic absorbent.

4. A process in accordance with claim 1 wherein the acids are removed from the maleic anhydride-lean effluent to obtain a purified recycle stream containing less than 7 ppm acids.

* * * * *